US006316481B1

(12) United States Patent
Freehauf

(10) Patent No.: US 6,316,481 B1
(45) Date of Patent: Nov. 13, 2001

(54) PHARMACEUTICAL COMPOSITION CONTAINING PROTON PUMP INHIBITORS

(75) Inventor: Keith Freehauf, Roselle Park, NJ (US)

(73) Assignee: Merck & Co. Inc., Rahway, NJ (US)

( * ) Notice: Subject to any disclaimer, the term of this patent is extended or adjusted under 35 U.S.C. 154(b) by 0 days.

(21) Appl. No.: 09/510,312

(22) Filed: Feb. 22, 2000

Related U.S. Application Data

(60) Provisional application No. 60/121,253, filed on Feb. 23, 1999.

(51) Int. Cl.$^7$ .................................................. A61K 31/415
(52) U.S. Cl. .............................. 514/393; 514/394
(58) Field of Search ...................... 514/393, 394

(56) References Cited

U.S. PATENT DOCUMENTS

| | | |
|---|---|---|
| 4,255,432 | 3/1981 | Kluge et al. . |
| 5,708,017 | 1/1998 | Dave et al. . |
| 5,731,002 | 3/1998 | Olovson et al. . |

FOREIGN PATENT DOCUMENTS

| | | |
|---|---|---|
| WO 88/06893 | 9/1988 | (WO) . |
| WO 94/25070 | 11/1994 | (WO) . |

*Primary Examiner*—Kevin E. Weddington
(74) *Attorney, Agent, or Firm*—Shu Muk Lee; David L. Rose

(57) ABSTRACT

The present invention is concerned with an oral pharmaceutical formulation containing a proton pump inhibitor (PPI) which is suitable for the treatment of gastric acid related diseases in man and animals. More specifically, the composition is a paste, and is particularly suitable for delivery of a proton pump inhibitor to horses.

11 Claims, No Drawings

PHARMACEUTICAL COMPOSITION CONTAINING PROTON PUMP INHIBITORS

This appln claims benefit of Prov. No. 60/121,253 filed Feb. 23, 1999.

SUMMARY OF THE INVENTION

The present invention relates to an improved oral paste formulation of omeprazole.

BACKGROUND OF THE INVENTION

Omeprazole is a potent inhibitors of gastric acid secretion that acts by inhibiting $H^+K^+$-ATPase, the enzyme involved in the final step of hydrogen ion production in the parietal cells, and has been used in the treatment of gastric acid related diseases, such as gastric and duodenal ulcers, in humans. Peptic ulcers are common also in some animals, particularly in horses. Although the etiology of gastro-duodenal ulcers in horses has not been ascertained, it appears that stress plays an important roles in some cases.

Omeprazole is highly acid labile and hence oral formulations are enteric-coated. Enteric coated formulations are expensive and time consuming to manufacture, and requires elaborate technology and equipment. Another disadvantage of enteric coated formulation is its moisture sensitivity.

WO94/25070 discloses oral composition containing a proton pump inhibitor in the form of enteric coated dry particles mixed with a dry gelling agent, the mixture may then be made into a paste-like gel prior to administration. The composition therefore requires enteric coating, with the aforementioned disadvantages associated with such formulation. Furthermore, because such a moist gel is not stable during long-term storage at room temperature it cannot be manufactured and sold as a ready-to-use formulation, rather it must be prepared ex tempore at the time of administration, making it inconvenient to use.

U.S. Pat. No. 5,708,017 describes paste formulations of proton-pump inhibitors comprising a proton-pump inhibitor, a thickening agent, a basifying agent and a hydrophobic oily liquid vehicle.

DETAILED DESCRIPTION OF THE INVENTION

The present invention provides an improved paste formulation of omeprazole comprising:
(a) about 1% to about 60% w/w of omeprazole,
(b) about 0.1% to about 2% w/w of two to four basifying agents,
(c) about 1% to about 3% w/w of a thickening agent, and
(d) about 30% to about 95% w/w of a hydrophobic oily liquid vehicle comprising
    (i) a vegetable oil and
    (ii) triglycerides of medium chain fatty acids or propylene glycol diesters of medium chain fatty acids.

Omeprazole is disclosed in U.S. Pat. No. 4,255,432. The amount of omeprazole in the present invention is not particularly critical so long as the drug product remains a semi-solid preparation; generally up to about 60% w/w of omeprazole can be tolerated. Preferably the amount of omeprazole is about 50% w/w or less, and more preferably from about 30 to about 40% w/w.

Suitable basifying agents are for example pharmaceutically acceptable amine bases such as monoethanolamine, diethanolamine, triethanolamine, or salts of carboxylic acids such as sodium acetate, sodium citrate, potassium sorbate, sodium stearate and the like. Preferably one of the basifying agent is potassium sorbate, and one or two other basifying agents may be selected from an amine base such as monoethanolamine and a carboxylic acid salt such as sodium stearate. The basifying agents are present in an amount sufficient to provide a non-acidic environment for the acid-labile omeprazole; typically, the total amount of basifying agents is from about 0.1 to about 2% w/w, and preferably from about 1 to about 1.5% w/w.

The thickening agent may be any pharmaceutically acceptable thickener that are insoluble or practically insoluble in water; examples include silicone dioxide, waxes such as castor wax or hydrogenated castor oil, paraffin, cetostearyl alcohol, and the like. The preferred hydrophobic thickener is hydrogenated castor oil. The amount of thickening agent is approximately 0.5% to 10% w/w of the final composition; preferably, it is about 1 to 2% w/w.

The hydrophobic oily liquid vehicle comprises (i) a vegetable oil and (ii) triglycerides of medium chain fatty acids or propylene glycol diesters of medium chain fatty acids. Examples of vegetable oil include almond oil, cottonseed oil, olive oil, peanut oil, safflower oil, sesame oil, and soybean oil. The preferred vegetable oil is sesame oil. Medium chain fatty acids are those having carbon chain lengths of from eight to twelve; preferably the fatty acids are saturated fatty acids. Preferred triglycerides and propylene glycol diesters are capric/caprylic triglycerides and propylene glycol caprate/caprylate (also referred to as propylene glycol octanoate decanoate). Capric/caprylic triglycerides and propylene glycol caprate/caprylate are commercially available products such as those marketed under the Miglyol® tradename (Huls America, Inc., New Jersey). The more preferred hydrophobic oily liquid vehicle comprises sesame oil and propylene glycol caprate/caprylate (such as Miglyol® 840). The hydrophobic vehicle is present at approximately 30% to 95% w/w, depending on the amount of other excipients in the paste. Preferably the hydrophobic vehicle is present at about 50 to about 80% w/w. In the hydrophobic vehicle the ratio of the vegetable oil to the triglyceride may range from about 1:3 to about 5:1; preferably about 1:1 to about 2:1.

The present compositon may include additional ingredients commonly used in the formulation of human and veterinary medicines. For example, flavoring agents such as caramel, carrot, apple, cinnamon and sausage flavors; coloring agents such as iron oxide, titanium dioxide, aluminum lakes; sweeteners such as sugar, sodium saccharin; preservatives such as parabens; antioxidants such as BHT, BHA; dispersants such as calcium stearate, and viscosity regulating agents such as white wax or synthetic waxes such as glyceryl tribehenate, glyceryl trimyristate, hydrogenated coco-glycerides can be added.

The composition of the present invention may be prepared by dispersing omeprazole in powder form in the hydrophobic liquid vehicle containing any other excipients except the thickening agent. The thickening agent is then added to the mixture and mixed to achieve the desired consistency. The composition of the present invention may also be prepared by dispersing the excipients in the hydrophobic oily liquid vehicle, followed by addition of the thickening agent, and if needed additional vegetable oil to achieve the desired consistency; to the resultant mixture is added omeprazole in powder form and the entire mixture is mixed well to disperse the omeprazole. The paste formulation thus obtained may be used to fill dosing syringes, which may be used directly to adminster the active drug to an animal in need of treatment.

The omeprazole paste formulations of the present invention have improved properties over previously described omeprazole paste formulations. The present formulations have better chemical and physical stability profiles, and provide higher drug bioavailability.

The composition of the present invention are useful in the treatment of peptic ulcer diseases in humans or animals. It can be used to deliver omeprazole orally for systemic activity in animals. The composition can also be used for the delivery of omeprazole in human with difficulty of swallowing solid dosage forms such as enteric coated tablets and capsules. The composition may be administered directly into the mouth of an animal, such as a horse, in need of anti-ulcer therapy; preferably a paste dosing syringe is used to facilitate drug administration. The consistency of this paste is such that it can not easily drip out or be expelled once it is deposited on the dorsal part of the animal's tongue. The paste is practically free of air bubbles which enhances dosing accuracy. Another advantage of this formulation is that individualized doses can be administered.

The amount of the composition to be administered may vary according to the particular animal species to be treated, the severity of the disease, the physical condition of the afflicted animal, and other factors. A physician or veterinarian skilled in the art of ulcer treatment may readily determined the proper dosage for the specific host under treatment. In general, a dose range of from about 0.2 mg/kg to about 20 mg/kg may be used.

The following example is provided to more fully illustrate the invention, and shall not be construed as limiting the scope of the invention in any manner.

EXAMPLE 1

| Component | Percent w/w |
| --- | --- |
| omeprazole base | 37.0 |
| potassium sorbate | 0.20 |
| sodium stearate | 0.10 |
| calcium stearate | 1.0 |
| monoethanolamine | 0.10 |
| yellow iron oxide | 0.20 |
| cinnamon oil | 0.30 |
| hydrogenated castor oil | 1.25 |
| propylene glycol octanoate decanoate | 25.0 |
| sesame oil | qs |

Potassium sorbate (0.50 kg), calcium stearate (2.50 kg), sodium stearate (0.25 kg), and yellow iron oxide (0.50 kg) are added to a double cone blender and mixed to disperse powders. The resultant powder is passed through a 60 mesh screen and milled at high speed. This milled powder preblend is collected in a polyethylene bag for use in paste manufacturing.

In a suitably sized vertical screw semi-solid paste mixer are added propylene glycol octanoate decanoate (62.5 kg) and sesame oil (37.5 kg). The temperature of the liquid mixture is adjusted to below approximately 25° C., if necessary, and the mixing screw is turned on. With the lumpbreaker on, the milled powder preblend, monoethanolamine (0.25 kg), and cinnamon oil (0.75 kg) are added to the mixer. Next, hydrogenated castor oil (3.13 kg) is added to the mixer, and mixing is until the product temperature reaches 50±5° C. The mixing screw and the lumpbreaker are stopped and the batch in the vessel is held for 30±5 minutes to assure completion of the gelling process.

With cooling water on, the remaining sesame oil (49.6 kg) is added to the mixer. The mixing screw and lumpbreaker are turned on for approximately two minutes to disperse the materials and then stopped. Omeprazole powder (92.5 kg) is added to the mixer in 8–10 portions; after addition of each portion the mixer is turned on for a period sufficient to wet most of the powder and then turned off for the addition of the next portion. After all the omeprazole has been added, mixing is continued for an additional 10 minutes to fully disperse the omeprazole; then the lumpbreaker is turned on and mixing continues for an additional 10 minutes to assure complete homogeneity. The resultant paste is used for packaging into syringes.

What is claimed is:

1. A pharmaceutical formulation for oral administration comprising:
    (a) about 1% to about 60% w/w of omeprazole,
    (b) about 0.1% to about 2% w/w of two to four basifying agents,
    (c) about 1% to about 3% w/w of a thickening agent, and
    (d) a hydrophobic oily liquid vehicle comprising
        (i) a vegetable oil and
        (ii) triglycerides of medium chain fatty acids or propylene glycol diesters of medium chain fatty acids.

2. A composition of claim 1 wherein said thickening agent is hydrogenated castor oil.

3. A composition of claim 1 wherein said hydrophobic liquid vehicle comprises propylene glycol caprate/caprylate and a vegetable oil.

4. A composition of claim 1 wherein said hydrophobic liquid vehicle comprises sesame oil and triglycerides of medium chain fatty acids or propylene glycol diesters of medium chain fatty acids.

5. A composition of claim 1 wherein said hydrophobic liquid vehicle comprises propylene glycol caprate/caprylate and sesame oil.

6. A composition of claim 1 wherein one of the basifying agents is potassium sorbate.

7. A composition of claim 1 wherein the basifying agents are potassium sorbate, sodium stearate and monoethanolamine.

8. A composition of claim 1 wherein the amount of omeprazole is about 30 to about 40% w/w.

9. A composition of claim 1 wherein the total amount of basifying agents is from about 1 to about 1.5% w/w.

10. A composition of claim 1 wherein the amount of the hydrophobic oily liquid vehicle is about 30% to 90% w/w.

11. A composition of claim 1 wherein the amount of the hydrophobic oily liquid vehicle is about 50% to 80% w/w.

* * * * *